United States Patent [19]

Igari et al.

[11] Patent Number: 5,534,269

[45] Date of Patent: Jul. 9, 1996

[54] METHOD OF PRODUCING SUSTAINED-RELEASE PREPARATION

[75] Inventors: Yasutaka Igari, Kobe; Kazumichi Yamamoto, Nara; Kayoko Okamoto, Osaka; Yutaka Yamagata, Kobe, all of Japan

[73] Assignee: Takeda Chemical Industries, Ltd., Osaka, Japan

[21] Appl. No.: 270,838

[22] Filed: Jul. 5, 1994

[30] Foreign Application Priority Data

Jul. 5, 1993 [JP] Japan .................................. 5-165793
Apr. 20, 1994 [JP] Japan .................................. 6-081765

[51] Int. Cl.$^6$ .................................................. A61K 9/14
[52] U.S. Cl. ........................ 424/489; 424/85.4; 424/484; 514/2; 514/21; 514/964
[58] Field of Search .............................. 424/489, 85.4, 424/484; 514/2, 21, 964

[56] References Cited

U.S. PATENT DOCUMENTS 4,962,091 10/1990 Eppstein et al. .......................... 514/2

FOREIGN PATENT DOCUMENTS

| A-0251631 | 7/1988 | European Pat. Off. . |
| 0461630 | 12/1991 | European Pat. Off. . |
| 0473268 | 4/1992 | European Pat. Off. . |
| 9306872 | 4/1993 | WIPO . |
| WO-A-9315722 | 8/1993 | WIPO . |

OTHER PUBLICATIONS

A. Supersaxo et al., "Preformed porous microspheres for controlled and pulsed release of macro–molecules", Journal of Controlled Release, vol. 23, (1993), pp. 157–164.

*Primary Examiner*—Nathan M. Nutter
*Assistant Examiner*—Duc Truong
*Attorney, Agent, or Firm*—Foley & Lardner

[57] ABSTRACT

A method of producing a sustained-release preparation which includes permitting a water-soluble polypeptide to permeate into a biodegradable matrix in the aqueous solution. The production method of the present invention makes possible the permeation of a water-soluble polypeptide into a biodegradable matrix without bringing the water-soluble polypeptide into contact with an organic solvent. Hence the water-soluble polypeptide is prepared without affecting the water-soluble polypeptide bioactivity and is thus effective for use as a pharmaceutical.

19 Claims, 1 Drawing Sheet

METHOD OF PRODUCING SUSTAINED-RELEASE PREPARATION

FIELD OF THE INVENTION

The present invention relates to a sustained-release preparation comprising a water-soluble polypeptide penetrated in a biodegradable matrix.

BACKGROUND OF THE INVENTION

Proteins, also referred to as polypeptides, are known to exhibit various pharmacologic actions in vivo. Thanks to advances in genetic engineering and cell engineering technologies, some have been produced in large mounts for pharmaceutical application using organisms such as *Escherichia coli*, yeasts, animal cells and hamsters. Such protein pharmaceuticals include interferons (alpha, beta, gamma), interleukin 2, erythropoietin and granulocyte colony-stimulating factor (G-CSF). These proteins, however, since they have generally a short biological half-life, must be administered frequently, posing the significant physical burden of injection on patients. To solve this problem, various attempts have been made to develop sustained-release preparations. Since proteins represented by cytokines must be administered with great care while monitoring their therapeutic effect, there is a need for development of injectable sustained-release preparations, particularly microcapsular sustained-release preparations, that have a release duration of about 1 to 2 weeks. It is generally known, however, that proteins undergo denaturation and lose their bioactivity upon exposure to heat, organic solvents, strong shearing force etc. For example, an aqueous solution of a protein can rapidly lose its bioactivity when heated at 60° C. for 20 minutes. Bioactivity of a protein can decrease upon heating, even at a lower temperature of 50° C. for about 1 hour. Similarly, protein bioactivity is known to decrease in the presence of an organic solvent such as ethanol or dichloromethane.

WO93/06872 discloses a technology for preparing a pharmaceutical preparation comprising porous particles of a biodegradable polymer allowing osteogenic proteins to be released over an extended period of time; an osteogenic protein and autologous blood aggregate. In this technology, the active ingredient osteogenic protein is adsorbed to the particles just before administration, and autologous blood is added to form an aggregate, to control release. Sustained-release duration is about several weeks. This method is not commonly usable because it involves the use of autologous blood.

In the Journal of Controlled Release, Vol. 23, p. 157 (1993), A. Supersaxo et al. describe a technology in which a porous microsphere is prepared using a biodegradable polymer, after which it is permeated with a macromolecule, is permitted to permeate therein to incorporate it in the microsphere without bringing the macromolecule into contact with an organic solvent. Specifically, since the polylactic acid used is hydrophobic, 50% ethanol (an organic solvent) is first used to wet the microsphere. The ethanol is then replaced with water and then with a solution of a macromolecule.

Japanese Patent Unexamined Publication No. 32559/1993 (EP-A 473268) discloses a method of producing a pharmaceutical composition by dissolving pharmaceutical composition components and a bioactive substance in an organic solvent or uniformly dispersing pharmaceutical composition components and a bioactive substance in an organic solvent or aqueous medium, and then drying the solution or dispersion.

Although various attempts have been made to produce sustained-release preparations retaining the bioactivity of proteins etc., as stated above, no satisfactory sustained-release preparations have been obtained as to efficiency of drug permeation into matrix, suppression of initial drug burst, constant long-term drug release etc.

SUMMARY OF THE INVENTION

Accordingly, the present invention relates to:

(1) a method of producing a sustained-release preparation which comprises permitting a water-soluble polypeptide to permeate into a biodegradable matrix in an aqueous solution, (2) the method according to (1) above, wherein the biodegradable matrix is produced by mixing a biodegradable polymer and a water-soluble metal salt of an aliphatic carboxylic acid, (3) the method according to (2) above, wherein the aliphatic carboxylic acid is an aliphatic monocarboxylic acid, (4) the method according to (2) above, wherein the water-soluble metal salt is a polyvalent metal salt, (5) the method according to (1) above, comprising the step of drying the biodegradable matrix after the water-soluble polypeptide has aqueously permeated into the biodegradable matrix, (6) the method according to (5) above, wherein drying is freeze-drying, (7) the method according to (1) above, wherein the water-soluble polypeptide is a cytokine, (8) the method according to (7) above, wherein the cytokine is an interferon, (9) the method according to (1) above, wherein the biodegradable matrix is in a fine particle form,

(10) the method according to (1) above, wherein the biodegradable matrix is produced from a biodegradable polymer,

(11) the method according to (10) above, wherein the biodegradable polymer is an aliphatic polyester,

(12) the method according to (11) above, wherein the aliphatic polyester is a copolymer derived from an α-hydroxycarboxylic acid,

(13) the method according to (12) above, wherein the copolymer is a lactic acid—glycolic acid copolymer,

(14) a sustained-release preparation which is produced by permitting a water-soluble polypeptide to permeate into a biodegradable matrix,

(15) the sustained-release preparation which is produced by mixing a biodegradable polymer and a water-soluble metal salt of an aliphatic carboxylic acid, and permitting a water-soluble polypeptide to permeate into the resulting biodegradable matrix, and

(16) a sustained-release preparation according to (14) above, wherein the preparation is for injection.

The water-soluble polypeptide in the present invention preferably has a molecular weight of about 200 to 50,000, more preferably about 5,000 to 40,000.

Any water-soluble polypeptide is acceptable, as long as it acts as a hormone and is secreted internally in to the blood stream. Such water-soluble polypeptides include cytokines, hematopoietic factors, growth factors and enzymes.

Examples of cytokines include lymphokines and monokines. Examples of lymphokines include interferons (alpha, beta, gamma) and interleukins (IL-2 through IL-12). Examples of monokines include an interleukin (IL-1) and tumor necrosis factors.

Hematopoietic factors include erythropoietin, granulocyte colony-stimulating factor (G-CSF), macrophage colony-stimulating factor (M-CSF), thrombopoietin, platelet growth-stimulating factor and megakaryocyte potentiator.

Examples of growth factors include basic or acidic fibroblast growth factors (FGF), members of the family thereof (e.g., FGF-9) (Molecular and Cellular Biology, Vol. 13, No. 7, p. 4251 (1993)), nerve cell growth factor (NGF) or members of the family thereof, insulin-like growth factors (e.g., IGF-1, IGF-2), and bone growth factor (BMP) or members of the family thereof.

Examples of enzymes include superoxide dismutase (SOD) and tissue plasminogen activator (TPA).

In addition to the above substances, growth hormone, insulin, natriuretic peptide, gastrin, prolactin, adrenocorticotropic hormone (ACTH), thyroid-stimulating hormone (TSH), luteinizing hormone (LH), follicle-stimulating hormone (FSH), human chorionic gonadotropin (HCG), motilin, kallikrein, Reg protein which is related to regeneration of pancreas (Japanese Patent Examined Publication No. 132388/1989, FEBS Letter s, Vol. 272, p. 85 (1990)) etc. can be used as the water-soluble polypeptide of the present invention.

The water-soluble polypeptide may be naturally derived or produced by gene recombination.

The water-soluble polypeptide is not limited to the above-described water-soluble polypeptides. Specifically, the water-soluble polypeptide may have a sugar chain or not, and may have a number of sugar chains of different structures. The water-soluble polypeptide may also be a mutant, derivative (agonistic or antagonistic) or fragment of the above-described water-soluble polypeptide.

The water-soluble polypeptide is preferably a cytokine. The cytokine is exemplified by lymphokines and monokines. Examples of lymphokines include interferons (alpha, beta, gamma) and interleukins (IL-2 through IL- 12). Examples of monokines include an interleukin (IL-1) and tumor necrosis factor.

The water-soluble polypeptide is more preferably a lymphokine. Examples of lymphokines include interferons (alpha, beta, gamma) and interleukins (IL-2 through IL-12).

The water-soluble polypeptide is particularly preferably an interferon (alpha, beta, gamma).

In the present invention, the biodegradable matrix is preferably in a fine particle form. The biodegradable matrix may be of any particle size, as long as it passes through ordinary injection needles for ordinary subcutaneous or intramuscular injection, specifically about 0.1 to 300 μm, preferably about 1 to 150 μm, and more preferably about 2 to 100 μm.

A biodegradable matrix is produced from, for example, a biodegradable polymer, by a per se known method. The biodegradable matrix is preferably produced by mixing a biodegradable polymer and a water-soluble metal salt of an aliphatic carboxylic acid. Methods which can be used for this purpose include the in-water drying method, phase separation method and spray drying method described below, and modifications thereof.

(i) In-water Drying Method (w/o/w Method)

Water or an aqueous solution containing a water-soluble component is used as an internal aqueous phase. The water-soluble component is exemplified by inorganic salts (e.g., sodium chloride, sodium hydrogen phosphate, disodium hydrogen phosphate), sugars (e.g., mannitol, glucose, inulin), organic salts (e.g., sodium carbonate, magnesium carbonate, ammonium acetate) and amino acids (e.g., glycine, arginine, histidine). The water-soluble component concentration in the aqueous solution is, for example, about 0.1 to 10% (w/v), preferably about 0.5 to 5% (w/v). When the water-soluble component is sodium chloride, in particular, it is preferable to use 0.9% (w/v) physiological saline, for instance. Calcium carbonate etc., in place of the above-described water-soluble component, may be dispersed in the internal aqueous phase. Preferably, an aqueous solution containing a water-soluble metal salt of an aliphatic carboxylic acid is used as the internal aqueous phase. The concentration of the metal salt in the aqueous solution is normally about 10 to 90% (w/v), preferably about 20 to 80% (w/v), depending on the solubility of the metal salt.

Water or an aqueous solution containing a water-soluble component as described above is emulsified and dispersed in an organic solvent solution of a biodegradable polymer or copolymer synthesized from α-hydroxycarboxylic acid to yield a w/o emulsion. Although the biodegradable polymer concentration in the organic solvent solution varies depending on the molecular weight of the biodegradable polymer and the kind of organic solvent, it is selected over the range from about 0.01 to 90% (w/w), preferably about 0.1 to 80% (w/w), and more preferably about 1 to 70% (w/w).

The ratio of the water or aqueous solution containing the water-soluble component and the organic solvent solution of the biodegradable polymer is normally 1:1000 to 1:1 (v/v), preferably 1:100 to 1:5 (v/v), and more preferably 1:50 to 1:5 (v/v). This emulsification is achieved by known methods of dispersion using a turbine type mechanical stirrer, homogenizer etc.

The w/o emulsion thus prepared is added to another aqueous phase (external aqueous phase) to form a w/o/w emulsion, followed by evaporation of the solvent in the oil phase, to yield a biodegradable matrix. The oil phase solvent is evaporated by stirring using, for example, a turbine type mechanical stirrer. The volume of the aqueous phase is chosen over the range normally from about 1 to 10,000 times, preferably from about 2 to 5,000 times, and more preferably from about 5 to 2,000 times, the volume of the oil phase.

An emulsifier may be added to the external aqueous phase. The emulsifier may be any one, as long as it is capable of forming a stable o/w emulsion. Examples of such emulsifiers include anionic surfactants, nonionic surfactants, polyoxyethylene castor oil derivatives, polyvinylpyrrolidone, polyvinyl alcohol, carboxymethyl cellulose, lecithin, gelatin and hyaluronic acid. These may be used singly or in combination. The concentration of the emulsifier used may be chosen as appropriate over the range normally from about 0.001 to 20% (w/w), preferably from about 0.01 to 10% (w/w), and more preferably from about 0.05 to 5% (w/w). When calcium carbonate, in place of the water-soluble component, is dispersed in the internal aqueous phase, the calcium carbonate is dissolved by adding dilute hydrochloric acid to the external aqueous phase.

The external aqueous phase may be supplemented with a water-soluble metal salt of an aliphatic carboxylic acid, whether or not identical to the metal salt of an aliphatic carboxylic acid used in the internal aqueous phase. In this case, it is preferable to add the metal salt of an aliphatic carboxylic acid so that its concentration in the external aqueous phase is about 0.01 to 20% (w/w), more preferably about 0.1 to 10% (w/w). By changing the concentration of the metal salt of an aliphatic carboxylic acid in the external aqueous phase, elution of the metal salt of an aliphatic carboxylic acid from the biodegradable matrix can also be controlled.

The biodegradable matrix thus obtained is collected by centrifugation or filtration, after which it is repeatedly washed with distilled water in several cycles to remove the emulsifier etc. adhering to the matrix surface, is again dispersed in distilled water etc. and then freeze-dried.

The surface of the obtained biodegradable matrix is not smooth, having pores of various sizes, some of which reach the inside of the biodegradable matrix. The ratio by volume of these pores in the biodegradable matrix (porosity) can be determined by, for example, the compressive mercury injection method or the BET method. Porosity varies depending on internal aqueous phase components, concentrations thereof, ratio of internal aqueous phase solution and organic solvent solution of biodegradable polymer, ratio of external aqueous phase volume and oil phase volume, external aqueous phase temperature and other factors; different pore structures are seen in the biodegradable matrix.

The content of water-soluble metal salt of an aliphatic carboxylic acid in the biodegradable matrix is preferably about 0.01 to 10% (w/w), more preferably about 0.05 to 7% (w/w), and still more preferably about 0.1 to 5% (w/w), based on metal. The content of the water-soluble metal salt of an aliphatic carboxylic acid in the biodegradable matrix is determined on a basis metalic by atomic absorption and other methods.

(ii) In-water Drying Method (o/w Method)

In the present invention, a biodegradable matrix can also be produced without using an internal aqueous phase. In this method, a solution of a biodegradable polymer in an organic solvent is first prepared. In this operation, the biodegradable polymer concentration in the organic solvent solution varies depending on the molecular weight of the biodegradable polymer, the kind of the organic solvent and other factors, and is chosen over the range normally from about 0.01 to 90% (w/w), preferably from about 0.1 to 80% (w/w), and more preferably from about 1 to 70% (w/w).

Calcium carbonate may be added to, and dispersed in, the organic solvent solution of the biodegradable polymer. In this operation, the mount of calcium carbonate added is set so that the ratio by weight of calcium carbonate and biodegradable polymer is about 5:1 to 1:100, preferably about 1 to 1:10.

Preferably, a water-soluble metal salt of an aliphatic carboxylic acid is added to and dispersed in the organic solvent solution of the biodegradable polymer. The metal salt of an aliphatic carboxylic acid is added in such amounts that the weight ratio of the metal salt of an aliphatic carboxylic acid to the biodegradable polymer is about 5:1 to 1:100, preferably about 2:1 to 1:50, and more preferably about 1:1 to 1:10.

Next, the organic solvent solution thus prepared is added to an aqueous phase to form an o/w emulsion using a turbine type mechanical stirrer or the like, followed by evaporation of the solvent in the oil phase, to yield a biodegradable matrix. The volume of the aqueous phase is chosen over the range normally from about 1 to 10,000 times, preferably from about 2 to 5,000 times, and more preferably from about 5 to 2,000 times, the volume of the oil phase.

An emulsifier may be added to the external aqueous phase. The emulsifier may be any one, as long as it is capable of forming a stable o/w emulsion. Examples of such emulsifiers include anionic surfactants, nonionic surfactants, polyoxyethylene castor oil derivatives, polyvinylpyrrolidone, polyvinyl alcohol, carboxymethyl cellulose, lecithin, gelatin and hyaluronic acid. These may be used singly or in combination. The concentration of the emulsifier used may be chosen as appropriate over the range normally from about 0.001 to 20% (w/w), preferably from about 0.01 to 10v/o (w/w), and more preferably from about 0.05 to 5% (w/w). When calcium carbonate is added to, and dispersed in, the organic solvent solution of the biodegradable polymer, dilute hydrochloric acid is added to the external aqueous phase.

The external aqueous phase may be supplemented with a water-soluble metal salt of an aliphatic carboxylic acid, whether or not identical to the metal salt of an aliphatic carboxylic acid added to and dispersed in the organic solvent solution of the biodegradable polymer. In this case, it is preferable to add the metal salt of an aliphatic carboxylic acid so that its concentration in the external aqueous phase is about 0.01 to 20% (w/w), more preferably about 0.1 to 10% (w/w). By changing the concentration of the metal salt of an aliphatic carboxylic acid in the external aqueous phase, elation of the metal salt of an aliphatic carboxylic acid from the biodegradable matrix can be controlled.

Alternatively, a biodegradable matrix can be produced by adding an organic solvent solution of a biodegradable polymer to an external aqueous phase containing a water-soluble metal salt of an aliphatic carboxylic acid to form an o/w emulsion in the same manner as above.

The biodegradable matrix thus obtained is collected by centrifugation or filtration, after which it is repeatedly washed with distilled water in several cycles to remove the emulsifier etc. adhering to the biodegradable matrix surface, is again dispersed in distilled water etc. and then lyophilized.

The content of water soluble metal salt of an aliphatic carboxylic acid in the biodegradable matrix is preferably about 0.01 to 10% (w/w), more preferably about 0.05 to 7% (w/w), and still more preferably about 0.1 to 5% (w/w), based on metal.

(iii) Phase Separation Method (Coacervation Method)

In producing a biodegradable matrix by the phase separation method, a coacervating agent is added little by little to the above-described w/o emulsion or organic solvent solution of a biodegradable polymer during stirring, to separate and solidify the biodegradable polymer. The coacervating agent is added in an mount by volume of about 0.01 to 1,000 times, preferably about 0.05 to 500 times, and more preferably about 0.1 to 200 times, the volume of the w/o emulsion or organic solvent solution of the biodegradable polymer.

Any coacervating agent is acceptable, as long as it is a polymer, mineral oil or vegetable oil compound that is miscible in the solvent for the biodegradable polymer and that does not dissolve the polymer. Examples of coacervating agents include silicon oil, sesame oil, soybean oil, corn oil, cotton seed oil, coconut oil, linseed oil, mineral oil, n-hexane and n-heptane. These may be used singly or in combination.

The biodegradable matrix thus obtained is collected by filtration, after which it is repeatedly washed with heptane etc. to remove the coacervating agent. The biodegradable matrix is then washed in the same manner as in the aqueous drying method and then lyophilized.

Solvent removal can be achieved by known methods, including the method in which the solvent is evaporated under normal or gradually reduced pressure during stirring using a propeller stirrer, magnetic stirrer or the like, and the method in which the solvent is evaporated while the degree of vacuum is adjusted using a rotary evaporator or the like.

The content of the water-soluble metal salt of the aliphatic carboxylic acid in the biodegradable matrix is preferably about 0.01 to 10% (w/w), more preferably about 0.05 to 7% (w/w), and still more preferably about 0.1 to 5% (w/w), based on metal.

In production by the in-water drying method or coacervation method, an antiflocculant may be added to prevent particle flocculation. The antiflocculant is exemplified by water-soluble polysaccharides such as mannitol, lactose, glucose, starches (e.g., corn starch), hyaluronic acid or alkali metal salts thereof, proteins such as glycine, fibrin and collagen, and inorganic salts such as sodium chloride and sodium hydrogen phosphate.

(iv) Spray Drying Method

In producing a biodegradable matrix by the spray drying method, (a) a w/o emulsion comprising water or an aqueous solution containing a water-soluble component and a biodegradable polymer or (b) an organic solvent solution of a biodegradable polymer are sprayed via a nozzle into the drying chamber of a spray drier to volatilize the organic solvent in the fine droplets in a very short time, to yield fine biodegradable capsules. The nozzle is exemplified by the double-fluid nozzle, pressure nozzle and rotary disc nozzle. To prevent biodegradable matrix flocculation where desired, an aqueous solution of the above-described antiflocculant may be effectively sprayed via another nozzle while spraying (a) the w/o emulsion comprising water or aqueous solution containing the water-soluble component and the biodegradable polymer or (b) the organic solvent solution of the biodegradable polymer. The biodegradable matrix is preferably produced by using a w/o emulsion comprising an aqueous solution containing a water-soluble metal salt of an aliphatic carboxylic acid and a biodegradable polymer or an organic solution of suspension of a biodegradable polymer containing a water-soluble metal salt of an aliphatic carboxylic acid. The biodegradable matrix thus obtained may have the water and organic solvent removed at increased temperature under reduced pressure when necessary.

The amount of organic solvent remaining in the biodegradable matrix used for the present invention is normally less than about 1,000 ppm, preferably less than about 500 ppm, more preferably less than 250 ppm and most preferably less than 100 ppm.

The starting material for the biodegradable matrix in the present invention is preferably a biodegradable polymer. Examples of biodegradable polymers include high molecular polymers insoluble or sparingly soluble in water, such as aliphatic polyesters (e.g., polymers, copolymers or mixtures thereof produced from one or more of α-hydroxycarboxylic acids such as glycolic acid, lactic acid, hydroxybutyric acid, valine acid and leucine acid, hydroxydicarboxylic acids such as malic acid, hydroxytricarboxylic acids such as citric acid and others), poly-α-cyanoacrylic acid esters and polyamino acids (e.g., poly-γ-benzyl-L-glutamic acid), and mixtures thereof. Here, the type of polymerization may be random, block or graft.

The biodegradable polymer is preferably an aliphatic polyester (e.g., a polymer, copolymer or mixture thereof produced from one or more of α-hydroxycarboxylic acids such as glycolic acid, lactic acid and hydroxybutyric acid, hydroxydicarboxylic acids such as malic acid, hydroxytricarboxylic acids such as citric acid, and others).

Of the above-mentioned aliphatic polyesters, polymers or copolymers synthesized from one or more of α-hydroxycarboxylic acids (e.g., glycolic acid, lactic acid and hydroxybutyric acid) are preferred from the viewpoint of reliable biodegradability and biocompatibility. More preferably, the aliphatic polyester is a copolymer synthesized from one or more α-hydroxycarboxylic acids (e.g., glycolic acid, lactic acid, hydroxybutyric acid). Still more preferably, the aliphatic polyester is a copolymer (e.g., glycolic acid—lactic acid copolymer) produced from two or more of α-hydroxycarboxylic acids (e.g., glycolic acid, lactic acid, hydroxybutyric acid).

Also, the biodegradable polymer of the present invention is preferably one that allows water to penetrate and enlarge the biodegradable matrix by swelling in the absence of ethanol and other organic solvents, when produced by a known method and formed into a biodegradable matrix administrable using an ordinary injection needle.

Although the above-described α-hydroxycarboxylic acid may be of the D-, L- or D,L-configuration, it is preferable that the ratio of the D-/L-configuration (mol %) falls within the range from about 75/25 to 25/75. More preferred is a hydroxycarboxylic acid wherein the ratio of the D-/L-configuration (mol %) falls within the range from about 60/40 to 30/70.

Examples of copolymers of the above-described α-hydroxycarboxylic acid include copolymers of glycolic acid with another α-hydroxy acid, the α-hydroxy acid being preferably lactic acid, 2-hydroxybutyric acid, valine acid or leucine acid.

The α-hydroxycarboxylic acid copolymer is preferably a lactic acid—glycolic acid copolymer or a 2-hydroxybutyric acid—glycolic acid copolymer.

More preferably, the α-hydroxycarboxylic acid copolymer is a lactic acid—glycolic acid copolymer.

With respect to the lactic acid—glycolic acid copolymer, it is preferable that the content ratio (lactic acid/glycolic acid) be about 100/0 to 40/60, more preferably about 90/10 to 45/55, and more preferably about 60/40 to 45/55. The weight-average molecular weight of the above-described glycolic acid—lactic acid is preferably about 3,000 to 12,000, more preferably about 4,000 to 10,000. The rates of permeation of the water-soluble polypeptide into the biodegradable matrix produced using said copolymer, and of elimination of the biodegradable matrix after administration in vivo are affected by the combination of content ratio and weight-average molecular weight. When the elimination period after administration (e.g., subcutaneous administration) in vivo is about 2 weeks, and when there is no problem in water permeation into the biodegradable capsule, the combination of a content ratio (lactic acid/glycolic acid) of about 50/50 and a weight-average molecular weight of about 4,000 to 9,000, preferably about 5,000 to 9,000, for example, may be mentioned.

In the present invention, two lactic acid—glycolic acid copolymers of different compositions and weight-average molecular weights may be used in a mixture of optional ratio. Such mixtures include a mixture of a lactic acid—glycolic acid copolymer having a content ratio (lactic acid/glycolic acid) (mol %) of about 75/25 and a weight-average molecular weight of about 6,000, and another lactic acid—glycolic acid copolymer having a content ratio (lactic acid/glycolic acid) (mol %) of about 50/50 and a weight-average molecular weight of about 4,000. The mixing ratio by weight is preferably from about 25/75 to 75/25.

Also, the dispersity of the lactic acid—glycolic acid copolymer (weight-average molecular weight/number-average molecular weight) is preferably about 1.2 to 4.0. Greater preference is given to a copolymer wherein the dispersity is about 1.5 to 3.5. The present lactic acid—glycolic acid copolymer can be produced by a known process, such as the method described in Japanese Patent Unexamined Publication No. 28521/1986. It is preferable that the copolymer be produced by catalyst-free dehydration polymerization condensation.

With respect to the 2-hydroxybutyric acid—glycolic acid copolymer, it is preferable that glycolic acid account for about 10 to 75 mol % and 2hydroxybutyric acid for the remaining portion. More preferably, glycolic acid accounts for about 20 to 75 mol %, still more preferably about 30 to 70 mol %. The 2-hydroxybutyric acid—glycolic acid copolymer has a weight-average molecular weight of about 2,000 to 20,000, preferably about 3,000 to 10,000, more preferably about 4,000 to 8,000. The dispersity of the glycolic acid copolymer (weight-average molecular weight/number-average molecular weight) is preferably about 1.2 to 4.0. Greater preference is given to a copolymer wherein the dispersity is about 1.5 to 3.5. The present glycolic acid copolymer can be produced by a known process, such as that described in Japanese Patent Unexamined Publication No. 28521/1986 (process based on dehydration polymerization condensation in the absence of catalyst or in the presence of an organic solid acid catalyst). It is preferable that the copolymer be produced by catalyst-free dehydration polymerization condensation.

The above-described glycolic acid copolymer may be used in a mixture with polylactic acid. Although the polylactic acid may be of the D-configuration, L-configuration or a mixture thereof, it is preferable that the ratio of the D-/L-configuration (mol %) falls within the range from about 75/25 to 20/80. More preferred is a polylactic acid wherein the ratio of the D-/L-configuration (mol %) falls within the range from about 60/40 to 25/75, with greater preference given to a polylactic acid wherein the ratio of the D-/L-configuration (mol %) falls within the range from about 55/45 to 25/75. The polylactic acid preferably has a weight-average molecular weight of about 1,500 to 10,000. More preferred is a polylactic acid wherein the weight-average molecular weight falls within the range from about 2,000 to 8,000, with greater preference given to a polylactic acid wherein the weight-average molecular weight falls within the range from about 3,000 to 6,000. Also, the dispersity of the polylactic acid is preferably about 1.2 to 4.0, more preferably about 1.5 to 3.5.

For producing polylactic acid, two methods are known: ring-opening polymerization of lactide, a dimer of lactic acid, and dehydration polymerization condensation of lactic acid. For obtaining a polylactic acid of relatively low molecular weight for the present invention, direct dehydration polymerization condensation of lactic acid is preferred. This method is, for example, described in Japanese Patent Unexamined Publication No. 28521/1986.

When a glycolic acid copolymer and polylactic acid are used in a mixture, their mixing ratio falls within the range from about 10/90 to 90/10 (% by weight), preferably from about 20/80 to 80/20, more preferably from about 30/70 to 70/30.

In the present invention, the biodegradable polymer produced by catalyst-free dehydration polymerization condensation usually has a terminal carboxyl group.

A biodegradable polymer having a terminal carboxyl group is a polymer in which the number-average molecular weights by GPC determination and that by end-group determination almost agree.

To quantitate terminal carboxyl groups, about 1 to 3 g of the biodegradable polymer is dissolved in a mixed solvent of acetone (25 ml) and methanol (5 ml), and the solution is quickly titrated with a 0.05N alcoholic solution of potassium hydroxide during stirring at room temperature with phenolphthalein as an indicator to determine the terminal carboxyl group content; the number-average molecular weight is calculated from the following equation:

$$\text{Number-average molecular weight by end-group determination} = 20,000\, A/B$$

where A is the weight mass (g) of the biodegradable polymer, and B is the amount (ml) of the 0.05N alcoholic solution of potassium hydroxide added until the titration end point is reached.

This value is hereinafter referred to as number-average molecular weight by end-group determination.

For example, in the case of a polymer having a terminal carboxyl group, and produced from one or more α-hydroxy acids by catalyst-free dehydration polymerization condensation, the number-average molecular weight by GPC determination and the number-average molecular weight by end-group determination almost agree with each other. On the other hand, in the case of a polymer having no terminal carboxyl groups, and synthesized from a cyclic dimer by ring-opening polymerization using a catalyst, the number-average molecular weight by end-group determination is significantly higher than the number-average molecular weight by GPC determination. This difference makes it possible to clearly differentiate a polymer having a terminal carboxyl group from a polymer having no terminal carboxyl group.

While the number-average molecular weight by end-group determination is an absolute value, the number-average molecular weight by GPC determination is a relative value, that varies depending on various analytical conditions (e.g., kind of mobile phase, kind of column, reference substance, slice width chosen, baseline chosen etc.); it is therefore difficult to have an absolute numerical representation of the latter. However, the fact that the number-average molecular weight by GPC determination and the number-average molecular weight by end-group determination almost agree with each other means that the number-average molecular weight by end-group determination falls within the range from about 0.5 to 2 times, preferably from about 0.8 to 1.5 times, the number-average molecular weight by GPC determination. Also, the fact that the number-average molecular weight by end-group determination is significantly higher than the number-average molecular weight by GPC determination means that the number-average molecular weight by end-group determination is over about 2 times of the number-average molecular weight by GPC determination.

In the present invention, preference is given to a polymer wherein the number-average molecular weight by GPC determination and the number-average molecular weight by end-group determination almost agree with each other.

In the present specification, weight-average molecular weight and number-average molecular weight are those based on polystyrene obtained by gel permeation chromatography (GPC) with 9 polystyrenes as reference substances with respective weight-average molecular weights of 120,000, 52,000, 22,000, 9,200, 5,050, 2,950, 1,050, 580 and 162. Measurements were taken using a GPC column KF804Lx2 (produced by Shown Denko) and an RI monitor L-3300 (produced by Hitachi, Ltd.) with chloroform as a mobile phase.

The dispersity is calculated by the formula: (weight-average molecular weight/number-average molecular weight).

The water-soluble metal salt of an aliphatic carboxylic acid may be any one, without limitation, as long as it is soluble in water and does not adversely affect the living body.

The water-soluble metal salt of an aliphatic carboxylic acid is preferably a metal salt of an aliphatic carboxylic acid whose water solubility at normal temperature (about 20° C.) is over about 20 mg/ml, more preferably over about 100 mg/ml, and still more preferably over about 200 mg/ml.

With respect to the water-soluble metal salt of an aliphatic carboxylic acid, the an aliphatic carboxylic acid preferably has 2 to 9 carbon atoms. Aliphatic carboxylic acids include aliphatic monocarboxylic acids, aliphatic dicarboxylic acids and aliphatic tricarboxylic acids. These carboxylic acids may be saturated or unsaturated.

Examples of aliphatic monocarboxylic acids include saturated aliphatic monocarboxylic acids having 2 to 9 carbon atoms (e.g., acetic acid, propionic acid, butyric acid, valeric acid, caproic acid, enanthic acid, caprylic acid, pelargonic acid, caprynic acid) and unsaturated aliphatic monocarboxylic acids having 2 to 9 carbon atoms (e.g., acrylic acid, propionic acid, methacrylic acid, crotonic acid, isocrotonic acid).

Examples of aliphatic dicarboxylic acids include saturated aliphatic dicarboxylic acids having 2 to 9 carbon atoms (e.g., malonic acid, succinic acid, glutaric acid, adipic acid, pimelic acid) and unsaturated aliphatic dicarboxylic acids having 2 to 9 carbon atoms (e.g., maleic acid, fumaric acid, citraconic acid, mesaconic acid).

Examples of aliphatic tricarboxylic acids include saturated aliphatic tricarboxylic acids having 2 to 9 carbon atoms (e.g., tricarballylic acid, 1,2,3butanetricarboxylic acid).

These aliphatic carboxylic acids may have 1 or 2 hydroxyl groups. Such aliphatic carboxylic acids include glycolic acid, lactic acid, glyceric acid, tartronic acid, malic acid, tartaric acid and citric acid.

The aliphatic carboxylic acid is preferably an aliphatic monocarboxylic acid, more preferably a saturated aliphatic monocarboxylic acid having 2 to 9 carbon atoms, and still more preferably a saturated aliphatic monocarboxylic acid having 2 to 3 carbon atoms. Examples of particularly preferable aliphatic carboxylic acids include acetic acid.

The metal salt in the water-soluble metal salt of an aliphatic carboxylic acid is exemplified by salts of monovalent metals such as alkali metals (e.g., sodium, potassium) and copper (I) salts, and polyvalent metal salts such as salts of alkaline earth metals (e.g., calcium, magnesium), zinc (II) salt, iron (II, III) salts, copper (II) salts, tin (II, IV) salts and aluminum (II, III) salts.

The metal salt is preferably a polyvalent metal salt, more preferably a calcium salt or zinc salt.

Examples of water-soluble metal salts of an aliphatic carboxylic acid include sodium acetate, potassium acetate, calcium acetate, zinc acetate, sodium propionate, calcium propionate, sodium glycolate, zinc glycolate, sodium lactate, calcium lactate, zinc lactate, sodium tartrate, zinc tartrate and sodium citrate. More preferred water-soluble metal salts of aliphatic carboxylic acid include calcium acetate and zinc acetate.

A water-soluble metal salt of an aromatic carboxylic acid can be used in the same manner as a water-soluble metal salt of an aliphatic carboxylic acid. Examples of the water-soluble metal salt of an aromatic carboxylic acid include sodium benzoate, zinc benzoate, sodium salycylate and zinc salycylate.

The solvent used in the oil phase for the above-mentioned methods is preferably an organic solvent that dissolves the biodegradable matrix and has a boiling point not higher than 120° C. Such solvents include halogenated hydrocarbons (e.g., dichloromethane, chloroform, carbon tetrachloride), alcohols (e.g., ethanol, methanol) and acetonitrile. These may be used singly or in combination. The organic solvent is preferably dichloromethane or acetonitrile.

The sustained-release preparation of the present invention can be produced by permitting a water-soluble polypeptide to permeate into a biodegradable matrix in an aqueous solution. The sustained-release preparation (e.g., microcapsules) of the present invention can be produced by, for example, the following procedure. The sustained-release preparation thus produced is hereinafter also referred to as microcapsules.

1) An aqueous solution of a water-soluble polypeptide is prepared.

2) A biodegradable matrix is brought into contact with the aqueous solution of paragraph 1), which is permitted to permeate into the biodegradable matrix.

3) Where necessary, the water-soluble polypeptide which has not permeated the biodegradable matrix is separated from the biodegradable matrix (washing).

4) The sustained-release preparation (e.g., microcapsules), which is produced by permitting the water-soluble polypeptide to permeate into the biodegradable matrix, is dried.

To the above-described aqueous solution of water-soluble polypeptide, salts injectable in vivo such as inorganic salts (e.g., sodium chloride, sodium monohydrogen phosphate), organic salts (e.g., ammonium acetate) and amino acids (e.g., glycine, arginine, histidine) may be added to increase water-soluble polypeptide solubility or to maintain water-soluble polypeptide bioactivity.

These salts may be used in combination to obtain pH values near the drug's optimum. Although the aqueous solution is normally adjusted to neutral to weakly acidic pH, it may be adjusted to alkaline pH. The concentration of these salts is adjusted so that the tonicity of the aqueous solution of the water-soluble polypeptide is about 1/50 to 5 times, preferably about 1/25 to 3 times, that of physiological saline. Surfactants such as Tween 80 may be added. The surfactant is used at concentrations of about 0.0001 to 0.2% (w/v), preferably about 0.001 to 0.1% (w/v).

Serum albumin may be added to the aqueous solution of the water-soluble polypeptide. Such serum albumin addition increases the water-soluble polypeptide solubility and allows retention of the water-soluble polypeptide's bioactivity. Serum albumin may be previously mixed with the water-soluble polypeptide. The serum albumin added is preferably human serum albumin, and may be separated and purified from human blood or may be produced by gene engineering techniques. The mixing ratio (by weight) of the water-soluble polypeptide and serum albumin is, for example, about 1:1,000 to 100:1, preferably about 1:100 to 10:1.

Although the water-soluble polypeptide concentration in the aqueous solution is not subject to limitation, it is preferable that the concentration be as high as possible below the water-soluble polypeptide solubility for permeating the biodegradable matrix with the maximum possible mount of water-soluble polypeptide per unit weight. This solubility varies depending on salt concentration, temperature and the presence or absence of additives. It is generally known that the water-soluble polypeptide release pattern of a sustained-release preparation varies depending on the concentration of the water-soluble polypeptide permeating the biodegradable matrix; water-soluble polypeptide concentrations are selected from this viewpoint as well. The water-soluble polypeptide concentration is normally about 100 μg/ml to 500 mg/ml, preferably about 1 to 300 mg/ml, and more preferably about 1 to 100 mg/ml.

In case the biodegradable matrix is produced by mixing a biodegradable polymer and a water-soluble metal salt of an aliphatic carboxylic acid, when the aqueous solution of a water-soluble polypeptide is permitted to permeate into the biodegradable matrix, although the pH of the aqueous solution of a water-soluble polypeptide varies depending on the kind of water-soluble metal salt of an aliphatic carboxylic acid contained in the biodegradable matrix, the isoelectric point of the water-soluble polypeptide and other factors, it is preferably about 3 to 9, more preferably about 3 to 8. The pH can be adjusted as appropriate using an acid such as an inorganic acid (e.g., hydrochloric acid) or an organic acid (e.g., acetic acid) or an alkali such as an alkali metal hydroxide (e.g., sodium hydroxide). The amount of acid or alkali used for this purpose is chosen as appropriate according to the degree of ionization and the strength of the acid or alkali and desired pH. Preferable water-soluble metal salts of aliphatic carboxylic acid include sodium acetate, zinc acetate and calcium acetate, because they are capable of permeating a biodegradable matrix with an aqueous solution of a water-soluble polypeptide at nearly neutral pH level.

The permeation of a water-soluble polypeptide into a biodegradable matrix in an aqueous solution is achieved by, for example, mixing an aqueous solution of the water-soluble polypeptide with the biodegradable matrix.

The order of mixing the coacervation of the water-soluble polypeptide and the biodegradable matrix is optional, as long as the water-soluble polypeptide's bioactivity is retained. For example, the biodegradable matrix may be immersed in the aqueous solution of the water-soluble polypeptide, or the aqueous solution of the water-soluble polypeptide may be added to the biodegradable matrix.

The mixing ratio of the aqueous solution of the water-soluble polypeptide and the biodegradable matrix is set so that the aqueous solution of the water-soluble polypeptide is used in excess to thoroughly permeate the biodegradable matrix with the aqueous solution of the water-soluble polypeptide. In other words, the mixture is prepared so that the entire biodegradable matrix is immersed in the aqueous solution of the water-soluble polypeptide.

Although the ratio by weight of the aqueous solution of the water-soluble polypeptide and the biodegradable matrix cannot be definitely determined because the biodegradable matrix is of variable porosity, it is preferably about 1:10 to 20:1, more preferably about 1:5 to 10:1. It is common practice, however, to use a minimum necessary amount of the aqueous solution of the water-soluble polypeptide, to minimize loss of the precious water-soluble polypeptide, rather than to re-use the water-soluble polypeptide which has not permeated the biodegradable matrix. The aqueous solution of the water-soluble polypeptide and the biodegradable matrix are normally mixed using a vessel, preferably one showing little adsorption of water-soluble polypeptides, as exemplified by siliconized glass. Also preferred are alloys (stainless steel and titanium alloy) that are surface-treated without spoiling the water-soluble polypeptide bioactivity.

The mixing operation is achieved by, for example, adding the biodegradable matrix to the aqueous solution of the water-soluble polypeptide and keeping such standing, with or without gentle stirring such that the water-soluble polypeptide bioactivity is not lost. This operation may be performed under such vacuum pressure such that the aqueous solution of the water-soluble polypeptide is not excessively bubbled. This mixing operation is performed at temperatures at which water-soluble polypeptide bioactivity is not affected or the biodegradable polymer constituting the biodegradable matrix is not decomposed; normally at room temperature, preferably in a cold place. Specifically, the mixing temperature is about 1° to 30° C., preferably about 4° to 25° C. Duration of mixing ranges from several minutes to scores of hours preferably from several hours to scores of hours, depending on biodegradable matrix content, biodegradable polymer composition, molecular weight, temperature and other factors. Specifically, mixing is performed at about 4° C. for about 10 to 100 hours, or at about 25° C. for about 5 to 50 hours. This duration is optionally chosen, as long as the water-soluble polypeptide bioactivity is not lost and as long as the biodegradable polymer is not excessively hydrolyzed. In case the biodegradable matrix produced by mixing a biodegradable polymer and a water-soluble metal salt of an aliphatic carboxylic acid is used, the duration of mixing can be shortened. Specifically, mixing is performed at about 4° C. for about 0.5 to 24 hours, or at about 25° C. for about 0.5 to 5 hours.

The mixing operation may be followed by washing, as necessary. The washing operation removes the water-soluble polypeptide which has not permeated the biodegradable matrix. Various methods of washing can be used, including those that do not destroy the biodegradable matrix and those in which the water-soluble polypeptide which has permeated the biodegradable matrix does not permeate out of the biodegradable matrix, and retains its bioactivity. For example, a washing solution is added after completion of the mixing operation, followed by centrifugation or filtration to separate the microcapsules from the washing solution; this process is repeated. The washing solution for this operation is distilled water or an aqueous solution containing a salt (e.g., sodium hydrogen phosphate, sodium chloride) or sugar (e.g., mannitol). The washing solution is preferably an aqueous solution containing mannitol.

The microcapsules thus obtained are then dried. Methods of drying include freeze drying and vacuum drying, with preference given to freeze drying. An antiflocculant may be added to prevent grain flocculation during the drying operation. The antiflocculant is exemplified by water-soluble polysaccharides such as mannitol, lactose, glucose and starches (e.g., corn starch), mucopolysaccharides such as hyaluronic acid, proteins such as glycine, fibrin and collagen, inorganic salts such as sodium chloride and sodium hydrogen phosphate, and phospholipids such as lecithin.

In the drying operation, the drying temperature is optional, as long as the water-soluble polypeptide bioactivity is not affected and the microcapsules are not destroyed. Preferably, the heating temperature exceeds the glass transition temperature of the biodegradable polymer used, and causes no mutual adhesion of microcapsule particles. Glass transition temperature is defined as the intermediate glass transition temperature (Tmg) obtained by heating at a rate of about 10° or 20° C. per minute, using a differential scanning calorimeter (DSC). Preferably, the heating temperature is higher by about 2° to 10° C. than the glass transition temperature, specifically about 25° to 50° C., preferably about 30° to 45° C. Heating time is a range of hours, preferably within about 24 hours after the microcapsules have reached a given temperature, depending on the heating temperature, mount of microcapsules to be treated and other factors. Any method of heating can be used without limitation, as long as the microcapsules are uniformly heated. Such methods include heating in a constant-temperature chamber, and microwave heating. This drying operation makes it possible to suppress early release after microcapsule administration to warm-blooded animals.

In the present invention, the water-soluble polypeptide bioactivity is hardly affected during preparation, since no organic solvents are used in permeating the biodegradable matrix with the water-soluble polypeptide nor is excessive heating used. The organic solvent mentioned herein is exemplified by halogenated hydrocarbons, alcohols, acetonitriles and glacial acetic acid.

Using a water-soluble metal salt of an aliphatic carboxylic acid makes it possible to efficiently permeate a biodegradable matrix with a water-soluble polypeptide. When used as an injection, the sustained-release preparation of the present invention exhibits almost constant sustained-release property over a long period of time, i.e., from about 1 week to 1 month.

The water-soluble polypeptide content in the sustained-release preparation of the present invention is determined by separating and quantitating the water-soluble polypeptide contained in the microcapsules by chromatography, such as HPLC, or immunological assay, such as enzyme immunoassay, or by measuring the bioactivity of the separated water-soluble polypeptide when the sustained-release preparation is a microcapsule, for instance. The content ratio of the water-soluble polypeptide to the biodegradable polymer in the microcapsules is normally about 0.1 to 30% (w/w), preferably about 1 to 20% (w/w).

The sustained-release preparation of the present invention can be administered as microcapsules as such or in the form of various dosage forms of non-oral preparations (e.g., intramuscular, subcutaneous or visceral injections or indwellable preparations, nasal, rectal or uterine transmucosal preparations) or oral preparations (e.g., capsules (such as hard capsules and soft capsules), or solid preparations such as granules and powders or liquid preparations such as suspensions).

In the present invention, the sustained-release preparation is preferably used for injection. When the sustained-release preparation is a microcapsule, it can be prepared as an injectable preparation by, for example, suspending the microcapsules in water, along with a dispersing agent (e.g., surfactants such as Tween 80 and HCO-60, polysaccharides such as carboxymethyl cellulose, sodium alginate and sodium hyaluronate, and protamine sulfate, a preservative (e.g., methyl paraben, propyl paraben), an isotonizing agent (e.g., sodium chloride, mannitol, sorbitol, glucose), a local anesthetizing agent (e.g., xylocaine hydrochloride, chlorobutanol) etc., to yield an aqueous suspensions, or by dispersing it in a vegetable oil such as sesame oil or corn oil or middle-chain fatty acid triglyceride (e.g., Miglyol 812, H üls Aktiengesellschaft) with or without a phospholipid such as lecithin, to yield an oily suspension.

When the sustained-release preparation is microcapsules, its particle size is chosen over the range from about 0.1 to 300 μm, for instance, as long as the requirements concerning the degree of dispersion and needle passage are met, when it is used as an injectable suspension. Preferably, the particle size falls within the range from about 1 to 150 μm, more preferably from about 2 to 100 μm.

The above-described microcapsule can be prepared as a sterile preparation without limitation by the method in which the entire production process is sterile, the method in which a gamma ray is used as a sterilant, and the method in which an antiseptic is added.

With low toxicity, the sustained-release preparation of the present invention can be safely used in mammals (e.g., humans, bovines, swines, dogs, cats, mice, rats, rabbits).

Indications for the sustained-release preparation of the present invention varies according to the water-soluble polypeptide used. For example, the sustained-release preparation of the present invention is effective in the treatment or prevention of viral hepatitis (e.g., hepatitis C, HBe antigen positive chronic active hepatitis B), cancers (e.g., renal cancer and multiple myeloma) when the water-soluble polypeptide is interferon alpha, anemia (e.g., anemia during renal dialysis) when the water-soluble polypeptide is erythropoietin, neutropenia (e.g., during anticancer agent therapy) and infectious diseases when the water-soluble polypeptide is G-CSF, cancers (e.g., hemangioendothelioma) when the water-soluble polypeptide is IL-2, digestive ulcers when the water-soluble polypeptide is FGF, thrombocytopenia when the water-soluble polypeptide is FGF-9, senile dementia and neuropathy when the water-soluble polypeptide is NGF, thrombosis etc. when the water-soluble polypeptide is TPA, diabetes mellitus when the water-soluble polypeptide is insulin, and cancers when the water-soluble polypeptide is tumor necrosis factor.

Depending on the type and content of the water-soluble polypeptide, duration of water-soluble polypeptide release, target disease, subject animal and other factors, the dose of the sustained-release preparation may be set at levels such that the water-soluble polypeptide exhibits its pharmacologic action. The dose per administration of the water-soluble polypeptide is chosen as appropriate over the range from about 0.0001 mg to 10 mg/kg body weight for each adult, when the preparation is a 1-week preparation. More preferably, the dose may be chosen as appropriate over the range from about 0.0005 mg to 1 mg/kg body weight.

The dose per administration of the sustained-release preparation is chosen as appropriate over the range from about 0.0005 mg to 50 mg/kg body weight for each adult. More preferably, the dose may be chosen as appropriate over the range from about 0.0025 mg to 10 mg/kg body weight. Dosing frequency can be chosen as appropriate, e.g., once weekly or once every two weeks, depending on type, content and dosage form of the water-soluble polypeptide, duration of water-soluble polypeptide release, subject disease, subject animal and other factors.

Although the preparation of the present invention may be stored at normal temperatures or cold places, it is preferable to store it at a cold place. Normal temperatures and cold places mentioned herein are as defined by the Pharmacopoeia of Japan, specifically, 15° to 25° C. for normal temperatures and under 15° C. for cold places.

The present invention is hereinafter described in more detail by means of the following working examples and comparative examples, which are not to be construed as limitative. Figures in the % unit are percent weight/volume ratios, unless otherwise stated.

EXAMPLE 1

2.0 g of a lactic acid—glycolic acid copolymer (lactic acid/glycolic acid=50/50 by mol %, GPC weight-average molecular weight 5,400, GPC number-average molecular weight 2,900, number-average molecular weight by end-group determination 2,200, produced by Wako Pure Chemical) was dissolved in 5.3 g (4 ml) of dichloromethane. After 1 ml of physiological saline for injection, as an internal aqueous phase, was added, the mixture was stirred for about 30 seconds using a homogenizer (Polytron). This solution was poured into 500 ml of a 0.1% (w/w) aqueous solution of polyvinyl alcohol (EG- 40, produced by The Nippon Synthetic Chemical Industry, Co., Ltd.), previously adjusted to 18° C., followed by stirring in a turbine homomixer at 4,000 rpm to yield a w/o/w emulsion, that was then stirred at room temperature for 5 hours to volatilize the dichloromethane and solidify the oil phase, that was then collected via centrifugation at 2,000 rpm using a centrifuge (05PR-22, Hitachi, Ltd.). The precipitate was again dispersed in distilled water and centrifuged. After the collected lactic acid—glycolic acid copolymer matrix was re-dispersed in a small mount of distilled water, the dispersion was lyophilized to yield a powder.

$1.08 \times 10^9$ IU (International Unit) of interferon alpha (containing about 25 mg of human serum albumin) weighed in a polyethylene test tube was dissolved in 200 µl of distilled water. To this solution, 200 mg of the above biodegradable matrix was added. After being tightly sealed, the mixture was kept standing at 4° to 8° C. in a refrigerator for about 4 days. After this operation, 5 ml of distilled water was added, followed by gentle stirring for about 1 minute and subsequent centrifugation at about 2,000 rpm for 5 minutes and supernatant discarding. This series of operations was repeated for 3 cycles for washing. To the resulting microcapsules, 44 mg of D-mannitol was added and 2 ml of distilled water was added, followed by gentle stirring, to yield a dispersion that was then vacuum dried at 40° C. for 6 hours.

EXAMPLE 2

A lactic acid—glycolic acid copolymer matrix was obtained as a powder in the same manner as in Example 1.

$1.08 \times 10^9$ IU of interferon alpha (containing about 25 mg of human serum albumin) weighed in a polyethylene test tube was dissolved in 200 µl of distilled water. To this solution, 200 mg of the above biodegradable matrix was added. After being tightly sealed, the mixture was kept standing at 4° to 8° C. in a refrigerator for about 30 hours. After this operation, 5 ml of distilled water was added, followed by gentle stirring for about 1 minute and subsequent centrifugation at about 1,000 rpm for 5 minutes; the supernatant was then discarded. This series of operations was repeated for 3 cycles for washing. To the resulting microcapsules, 1 ml of a 0.1% aqueous solution of sodium hyaluronate (molecular weight 1,800,000) was added, followed by gentle stirring, to yield a dispersion that was then lyophilized for 16 hours.

EXAMPLE 3

4.0 g of a lactic acid—glycolic acid copolymer (lactic acid/glycolic acid=50/50 by mol %, GPC weight-average molecular weight 5,900, GPC number-average molecular weight 2,600, produced by Wako Pure Chemical) was dissolved in 5.3 g (4 ml) of dichloromethane. After 4 g of calcium carbonate was added, the solution was stirred for about 30 seconds using a vortex mixer, to yield an s/o emulsion. This emulsion was poured into 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield an s/o/w emulsion, which was then stirred at room temperature for 5 hours to volatilize the dichloromethane and solidify the oil phase. Then 10 ml of 1N hydrochloric acid was added to remove the excess amount of calcium carbonate. After centrifugation at about 2,000 rpm (05PR-22, Hitachi, Ltd.), the supernatant was discarded. The residue was again dispersed in distilled water and centrifuged. After the collected biodegradable matrix was re-dispersed in a small amount of distilled water, the dispersion was freeze-dried to yield a powder (about 2.0 g).

4 mg ($8 \times 10^8$ IU) of freeze-dried interferon alpha was weighed in a glass test tube and dissolved in 2 ml of 10 mM hydrochloric acid solution. To this solution, 50 mg of the above biodegradable matrix was added, followed by rotary mixing at 4° C. on a Low-Profile Roller (produced by Life Science) for about 1 day. After this operation, 4 ml of distilled water was added, followed by gentle stirring for about 1 minute and subsequent centrifugation at about 1,000 rpm for 5 minutes; the supernatant was then discarded. This series of operations were repeated for 2 cycles for washing. The resulting dispersion was freeze-dried to yield microcapsules (about 48 mg).

To determine the interferon alpha content in the obtained microcapsules, the microcapsules were extracted with a 25% solution of Block Ace (Snow Brand Milk Products Co., Ltd.) (blocking agent for immunological experiments) containing 10% acetonitrile and then subjected to EIA (enzyme immunoassay). Interferon alpha was contained in the microcapsules at 5,700,000 IU per mg microcapsule.

EXAMPLE 4

4.0 g of a lactic acid—glycolic acid copolymer (lactic acid/glycolic acid=50/50 by mol %, GPC weight-average molecular weight 5,100, GPC number-average molecular weight 2,570, produced by Wako Pure Chemical) was dissolved in 5.3 g (4 ml) of dichloromethane. After 0.4 g of zinc acetate (dihydrate) was added, the solution was shaken for 2 hours and then stirred for about 30 seconds using a homogenizer (Polytron), to yield an s/o emulsion. This emulsion was poured into 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield an s/o/w emulsion, that was then stirred at room temperature for 5 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected biodegradable matrix was re-dispersed in a small amount of distilled water, the dispersion was freeze-dried to yield a powder (about 2.0 g).

6 mg (about $1.2 \times 10^9$ IU) of freeze-dried interferon alpha was weighed in a glass test tube and dissolved in 3 ml of 0.5 mM hydrochloric acid solution. To this solution, 300 mg of the above biodegradable matrix was added, followed by rotary mixing at 4° C. on a Low-Profile Roller (produced by Life Science) for about 1 day. After this operation, 10 ml of a 5% aqueous solution of mannitol was added, followed by gentle stirring for about 1 minute and subsequent centrifugation at about 2,000 rpm for 5 minutes; the supernatant was then discarded. This series of operations was repeated for 3 cycles for washing. To the resulting microcapsules, 30 mg of D-mannitol and 0.5 ml of distilled water were added, followed by gentle stirring, to yield a suspension that was then freeze-dried to yield microcapsules (about 310 mg).

To determine the interferon alpha content in the obtained microcapsules, the microcapsules were extracted with a 25% solution of Block Ace (Snow Brand Milk Products Co., Ltd.) (blocking agent for immunological experiments) containing 10% acetonitrile and then subjected to enzyme immunoassay (sandwich technique using an interferon antibody, hereinafter abbreviated EIA). Interferon alpha was contained in the microcapsules at 2,300,000 IU per mg microcapsule.

EXAMPLE 5

4.0 g of a lactic acid—glycolic acid copolymer (lactic acid/glycolic acid=50/50 by mol %, GPC weight-average molecular weight 5,900, GPC number-average molecular weight 2,600, produced by Wako Pure Chemical) was dissolved in 5.3 g (4 ml) of dichloromethane. After 1 ml of an aqueous solution containing 800 mg of zinc acetate (dihydrate) was added, the solution was stirred for about 30 seconds using a homogenizer (Polytron), to yield a w/o emulsion. This emulsion was poured into 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield a w/o/w emulsion, which was then stirred at room temperature for 5 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected biodegradable matrix was re-dispersed in a small amount of distilled water, the dispersion was freeze-dried to yield a powder (about 2.0 g).

6 mg (about $1.2 \times 10^9$ IU) of freeze-dried interferon alpha was weighed in a glass test tube and dissolved in 3 ml of 0.5 mM hydrochloric acid solution. To this solution, 300 mg of the above biodegradable matrix was added, followed by rotary mixing at 10° C. on a Low-Profile Roller (produced by Life Science) for about 1 day. After this operation, 10 ml of a 5% aqueous solution of mannitol was added, followed by gentle stirring for about 1 hour and subsequent centrifugation at about 1,000 rpm for 5 minutes; the supernatant was then discarded. This series of operations was repeated for 2 cycles for washing. The resulting microcapsules were freeze-dried.

To determine the interferon alpha content in the obtained microcapsules, the microcapsules were extracted with a 25% solution of Block Ace (Snow Brand Milk Products Co., Ltd.) (blocking agent for immunological experiments) containing 10% acetonitrile and then subjected to EIA. Interferon alpha was contained in the microcapsules at 780,000 IU per mg microcapsule.

EXAMPLE 6

4.0 g of a lactic acid—glycolic acid copolymer (lactic acid/glycolic acid=50/50 by mol %, GPC weight-average molecular weight 5,900, GPC number-average molecular weight 2,600, produced by Wako Pure Chemical) was dissolved in 5.3 g (4 ml) of dichloromethane. After 0.4 g of calcium acetate (monohydrate) was added, the solution was stirred for about 30 seconds using a homogenizer (Polytron), to yield an s/o emulsion. This emulsion was poured into 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield an s/o/w emulsion, which was then stirred at room temperature for 5 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected biodegradable matrix was re-dispersed in a small amount of distilled water, the dispersion was freeze-dried to yield a powder (about 2.0 g).

4 mg ($8 \times 10^8$ IU) of freeze-dried interferon alpha was weighed in a glass test tube and dissolved in 2 ml of 1 mM hydrochloric acid solution. To this solution, 50 mg of the above biodegradable matrix was added, followed by rotary mixing at 4° C. on a Low-Profile Roller (produced by Life Science) for about 1 day. After this operation, 4 ml of distilled water was added, followed by gentle stirring for about 1 minute and subsequent centrifugation at about 1,000 rpm for 5 minutes; the supernatant was then discarded. This series of operations were repeated for 2 cycles for washing. The resulting dispersion was freeze-dried to yield microcapsules (about 48 mg).

To determine the interferon alpha content in the obtained microcapsules, the microcapsules were extracted with a 25% solution of Block Ace (Snow Brand Milk Products Co., Ltd.) (blocking agent for immunological experiments) containing 10% acetonitrile and then subjected to EIA. Interferon alpha was contained in the microcapsules at 9,400,000 IU per mg microcapsule.

EXAMPLE 7

4.0 g of a lactic acid—glycolic acid copolymer (lactic acid/glycolic acid=50/50 by mol %, GPC weight-average molecular weight 5,100, GPC number-average molecular weight 2,570, produced by Wako Pure Chemical) was dissolved in 5.3 g (4 ml) of dichloromethane. After 0.4 g of zinc acetate (dihydrate) was added, the solution was shaken for 2 hours and then stirred for about 30 seconds using a homogenizer (Polytron), to yield an s/o emulsion. This emulsion was poured into 800 ml of a 0.1% (w/w) aqueous solution of polyvinyl alcohol (EG-40, produced by The Nippon Synthetic Chemical Industry, Co., Ltd.) previously adjusted to 18° C., followed by stirring in a turbine homomixer at 6,000 rpm to yield an s/o/w emulsion, which was then stirred at room temperature for 5 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected biodegradable matrix was re-dispersed in a small mount of distilled water, the dispersion was freeze-dried to yield a powder (about 2.0 g).

50 mg of the biodegradable matrix was weighed in a glass test tube. After a 2 mg/ml interferon alpha solution (about $4.0 \times 10^8$ IU), previously adjusted to appropriate pH with hydrochloric acid or sodium hydroxide (four pH levels of about 2, 4, 5 and 8) was added, the mixture was subjected to rotary mixing at 4° C. for 24 hours, to permit the interferon alpha to permeate the biodegradable matrix. After centrifugation at about 1,000 rpm and supernatant removal, the residue was twice washed with 4 ml of distilled water, followed by addition of 0.5 ml of distilled water and freeze-drying.

EXAMPLE 8

4.0 g of a lactic acid—glycolic acid copolymer (lactic acid/glycolic acid=50/50 by mol %, GPC weight-average molecular weight 5,900, GPC number-average molecular weight 2,600, produced by Wako Pure Chemical) was dissolved in 5.3 g (4 ml) of dichloromethane. After 0.4 g of calcium acetate (monohydrate) was added, the solution was stirred for about 30 seconds using a homogenizer (Polytron), to yield an s/o emulsion. This emulsion was poured into 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield an s/o/w emulsion, which was then stirred at room temperature for 5 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected biodegradable matrix was re-dispersed in a small amount of distilled water, the dispersion was freeze-dried to yield a powder (about 4.0 g).

Next, interferon alpha was permitted to permeate into the biodegradable matrix at various pH levels, followed by freeze-drying, in the same manner as in Example 7.

EXAMPLE 9

4.0 g of a lactic acid—glycolic acid copolymer (lactic acid/glycolic acid=50/50 by mol %, GPC weight-average molecular weight 5,100, GPC number-average molecular weight 2,570, produced by Wako Pure Chemical) was dissolved in 5.3 g (4 ml) of dichloromethane. After 0.2 g of sodium acetate (trihydrate) was added, the solution was shaken for 2 hours and then stirred for about 30 seconds using a homogenizer (Polytron), to yield an s/o emulsion. This emulsion was poured into 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield an s/o/w emulsion, which was then stirred at room temperature for 5 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected biodegradable matrix was re-dispersed in a small amount of distilled water, the dispersion was freeze-dried to yield a powder (about 2.0 g).

Next, interferon alpha was permitted to permeate into the biodegradable matrix at various pH levels, followed by freeze-drying, in the same manner as in Example 7.

EXAMPLE 10

4.0 g of a lactic acid—glycolic acid copolymer (lactic acid/glycolic acid=50/50 by mol %, GPC weight-average molecular weight 5,100, GPC number-average molecular weight 2,570, produced by Wako Pure Chemical) was dissolved in 5.3 g (4 ml) of dichloromethane. After 0.4 g of zinc acetate (dihydrate) was added, the solution was shaken for 2 hours and then stirred for about 30 seconds using a homogenizer (Polytron), to yield an s/o emulsion. This emulsion was poured into 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield an s/o/w emulsion, which was then stirred at room temperature for 5 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected biodegradable matrix was re-dispersed in a small amount of distilled water, the dispersion was freeze-dried to yield a powder (about 2.0 g).

2 ml of an aqueous solution containing interleukin 2 (20 µg) was taken in a glass test tube. After 300 mg of the above biodegradable matrix was added, the mixture was subjected to rotary mixing at 4° C. for about 5 hours on a Low-Profile Roller (produced by Life Science). The interleukin 2 was produced by the method described in Japanese Patent Unexamined Publication No. 78799/1986 and purified by the method described in Japanese Patent Unexamined Publication No. 115528/1985. The interleukin 2 was a mixture of one with methionine bound to the N-terminal, and the other without methionine. After this operation, 10 ml of a 5% aqueous solution of mannitol was added, followed by gentle stirring for about 1 minute and subsequent centrifugation at about 2,000 rpm for 5 minutes; the supernatant was then discarded. This series of operations was repeated in 3 cycles for washing. To the obtained microcapsules, 30 mg of D-mannitol was added; the mixture was dissolved in 0.5 ml of distilled water, followed by gentle stirring. The resulting suspension was freeze-dried.

EXAMPLE 11

5.0 g of a lactic acid—glycolic acid copolymer (lactic acid/glycolic acid=50/50 by mol %, GPC weight-average molecular weight 5,800, GPC number-average molecular weight 2,805, produced by Wako Pure Chemical) and 782 mg of zinc benzoate were added to 6.625 g (5 ml) of dichloromethane, and shaken for 3 hours at room temperature to yield an s/o emulsion. This emulsion was poured into 1,000 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield an s/o/w emulsion, that was then stirred at room temperature for 5 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected biodegradable matrix was re-dispersed in a small amount of distilled water, the dispersion was freeze-dried to yield a powder (about 2.0 g).

2 mg (about $1.7 \times 10^8$ IU) of freeze-dried interferon alpha was weighed in a glass test tube and dissolved in 3 ml of 0.5 mM hydrochloric acid solution. To this solution, 302 mg of the above biodegradable matrix was added, followed by rotary mixing at 15° C. on a Low-Profile Roller (produced by Life Science) for about 5 hours. After this operation, 10 ml of a 5% aqueous solution of mannitol was added, followed by gentle stirring for about 1 minute and subsequent centrifugation at about 2,000 rpm for 5 minutes; the supernatant was then discarded. This series of operations was repeated for 3 cycles for washing. To the resulting microcapsules, 30 mg of D-mannitol and 0.5 ml of distilled water were added, followed by gentle stirring, to yield a suspension that was then freeze-dried to yield microcapsules (about 310 mg).

To determine the interferon alpha content in the obtained microcapsules, the microcapsules were extracted with a 25% solution of Block Ace (Snow Brand Milk Products Co., Ltd.) (blocking agent for immunological experiments) containing 10% acetonitrile and then subjected to EIA. Interferon alpha was contained in the microcapsules at 3,610,000 IU per mg microcapsule.

EXAMPLE 12

A lactic acid—glycolic acid copolymer matrix was obtained as a powder in the same manner as in Example 11 except that 995 mg of zinc salycylate was substituted for the zinc benzoate. And then microcapsules were obtained in the same manner as in Example 11 except that 304 mg of the matrix was used.

Interferon alpha was contained in the microcapsules at 1,930,000 IU per mg microcapsules.

COMPARATIVE EXAMPLE 1

2 mg of freeze-dried powder interferon alpha was dissolved in 2 ml of a phosphate-buffered saline containing 0.5% bovine albumin (175,000,000 IU/ml concentration as determined by EIA).

COMPARATIVE EXAMPLE 2

4.0 g of a lactic acid—glycolic acid copolymer (lactic acid/glycolic acid=50/50 by mol %, GPC weight-average molecular weight 5,900, GPC number-average molecular weight 2,600, produced by Wako Pure Chemical) was dissolved in 5.3 g (4 ml) of dichloromethane. After addition of 0.5 ml of an aqueous solution of zinc chloride, previously adjusted to a concentration of 2 g/ml, the solution was stirred for about 30 seconds, via homogenizer (Polytron) to yield a w/o emulsion. This emulsion was poured into 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield a w/o/w emulsion, which was then stirred at room temperature for 5 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected biodegradable matrix was re-dispersed in a small amount of distilled water, the dispersion was freeze-dried to yield a powder (about 2.0 g).

Next, interferon alpha was permitted to permeate into the biodegradable matrix at various pH levels, followed by freeze-drying, in the same manner as in Example 7.

COMPARATIVE EXAMPLE 3

4.0 g of a lactic acid—glycolic acid copolymer (lactic acid/glycolic acid=50/50 by mol %, GPC weight-average molecular weight 5,900, GPC number-average molecular weight 2,600, produced by Wako Pure Chemical) was dissolved in 5.3 g (4 ml) of dichloromethane. After 0.2 g of zinc carbonate was added, the solution was stirred for about 30 seconds using a vortex mixer, to yield an s/o emulsion. This emulsion was poured into 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield an s/o/w emulsion, which was then stirred at room temperature for 5 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected biodegradable matrix was re-dispersed in a small amount of distilled water, the dispersion was freeze-dried to yield a powder (about 2.0 g).

Next, interferon alpha was permitted to permeate into the biodegradable matrix at various pH levels, followed by freeze-drying, in the same manner as in Example 7.

EXPERIMENTAL EXAMPLE 1

About 40 mg of microcapsules as obtained in Example 1 were dispersed in 0.5 ml of a dispersant (distilled water containing 2.5 mg of carboxymethyl cellulose, 0.5 mg of polysorbate 80 and 25 mg of mannitol, all dissolved therein) to yield an injectable preparation that was subcutaneously administered to the back of 8-week-old male SD rats using a 22-gauge needle (microcapsule dose 133 mg/kg). After administration, blood was collected via the tail at constant intervals and assayed for serum interferon alpha concentration by enzyme immunoassay (EIA). Almost constant blood concentration was sustained for 1 week.

EXPERIMENTAL EXAMPLE 2

About 30 mg of microcapsules as obtained in Example 2 was administered to rats in the same manner as in Experimental Example 1, and serum interferon alpha concentrations were determined by enzyme immunoassay (EIA). Almost constant blood concentration was sustained for 1 week.

EXPERIMENTAL EXAMPLE 3

About 22 mg of microcapsules as obtained in Example 4 and about 64 mg of microcapsules as obtained in Example 5 were each dispersed in 0.5 ml of a dispersant (5 g of carboxymethyl cellulose, 2 g of polysorbate 80 (surfactant) and 25 g of mannitol, all dissolved in 1 liter of distilled water) to yield an injectable preparation that was subcutaneously administered to the backs of 8-week-old male SD rats using an 18-gauge needle (interferon alpha administered at about 50,000,000 IU per rat). After administration, blood was collected via the tail at constant intervals and assayed for serum interferon alpha concentration by EIA. For control, an aqueous solution of interferon alpha as obtained in Comparative Example 1 was subcutaneously administered to rats (interferon alpha administered at about 50,000,000 IU per rat). In the group dosed with the microcapsules of Comparative Example 1, the serum interferon level fell to the detection limit by 3 days after administration. In the groups dosed with the microcapsules of Example 4 or 5, an initial high blood concentration was followed by almost constant blood concentrations sustained for 1 week.

EXPERIMENTAL EXAMPLE 4

The effects of interferon alpha solution pH and various zinc salts on the efficiency of interferon alpha permeation in the biodegradable matrix (interferon content in the microcapsules) were examined as follows.

Microcapsules as obtained in Example 7 (zinc acetate), Comparative Example 2 (zinc chloride) and Comparative Example 3 (zinc carbonate) were each extracted with a 25% solution of Block Ace containing 10% acetonitrile and then subjected to EIA to determine the interferon alpha content. As shown in FIG. 1, interferon alpha permeation efficiency was high with pH conditions under which interferon alpha is relatively physically stable, when zinc acetate was used.

EXPERIMENTAL EXAMPLE 5

The effects of interferon alpha solution pH and calcium acetate salt on the efficiency of interferon alpha permeation into the biodegradable matrix (interferon content in the microcapsules) were examined in the same manner as in Experimental Example 3. As shown in FIG. 2, interferon alpha permeation efficiency was high with such pH conditions under which interferon alpha is relatively physically stable.

EFFECT OF THE INVENTION

According to the production method of the present invention, it is possible to permeate a biodegradable matrix with a water-soluble polypeptide without bringing the water-soluble polypeptide into contact with an organic solvent, and to prepare the water-soluble polypeptide as a pharmaceutical preparation without affecting the water-soluble polypeptide bioactivity. Also, use of a metal salt of an aliphatic carboxylic acid makes it possible to efficiently permeate a biodegradable matrix with a water-soluble polypeptide. The sustained-release preparation of the present invention exhibits an excellent sustained-release property over several days to one month (e.g., about 1 to 2 weeks) when used as an injection.

Figure 1:
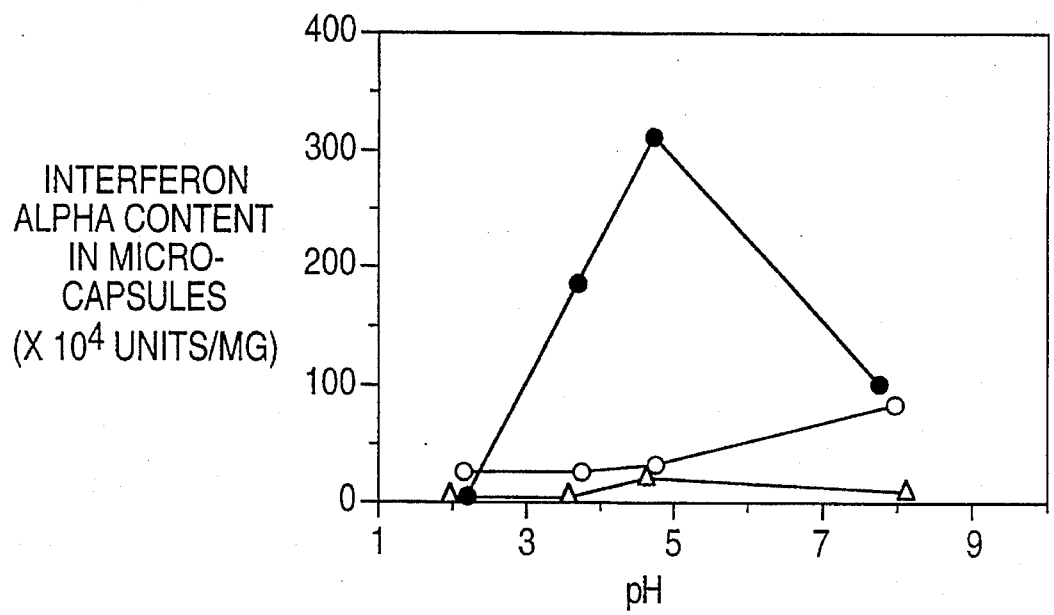
FIG. 1 shows the relation between interferon solution pH and various zinc salts and the interferon content in the microcapsules, in which ● represents zinc acetate (Example 7), ○ zinc chloride (Comparative Example 2), and Δ zinc carbonate (Comparative Example 3).
Figure 2:
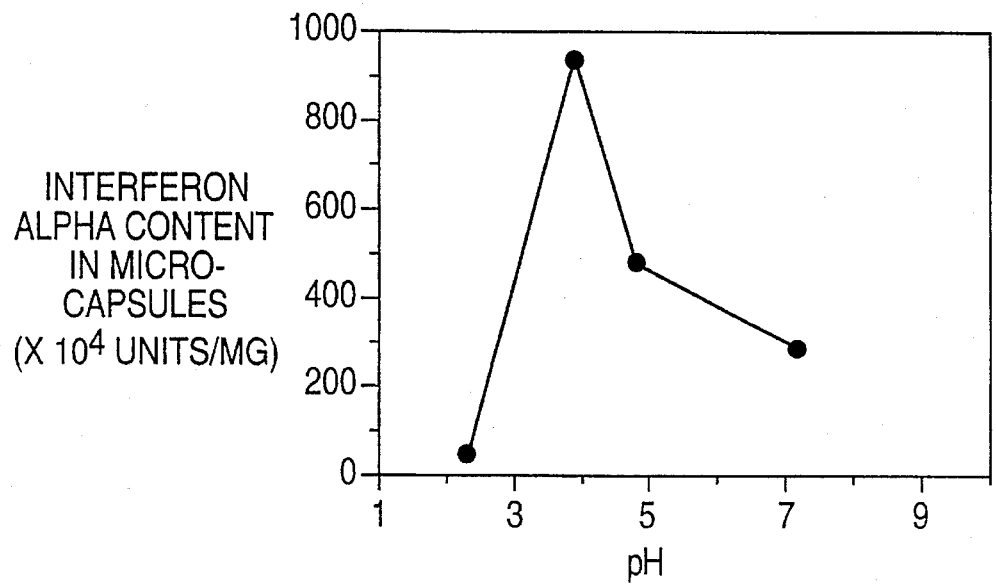
FIG. 2 shows the relation between interferon solution pH and calcium acetate (Example 5) and interferon content in the microcapsules.

What we claim is:

1. A method of producing a sustained-release preparation which comprises permitting a water-soluble polypeptide in an aqueous solution to permeate into a biodegradable matrix.

2. The method according to claim 1, wherein the biodegradable matrix is produced by mixing a biodegradable polymer and a water-soluble metal salt of an aliphatic carboxylic acid.

3. The method according to claim 2, wherein the aliphatic carboxylic acid is an aliphatic monocarboxylic acid.

4. The method according to claim 2, wherein the water-soluble metal salt is a polyvalent metal salt.

5. The method according to claim 1, comprising the step of drying the biodegradable matrix after the water-soluble polypeptide has aqueously permeated into the biodegradable matrix.

6. The method according to claim 5, wherein drying is freeze-drying.

7. The method according to claim 1, wherein the water-soluble polypeptide is a cytokine.

8. The method according to claim 7, wherein the cytokine is an interferon.

9. The method according to claim 1, wherein the biodegradable matrix is in a fine particle form.

10. The method according to claim 1, wherein the biodegradable matrix is produced from a biodegradable polymer.

11. The method according to claim 10, wherein the biodegradable polymer is an aliphatic polyester.

12. The method according to claim 11, wherein the aliphatic polyester is a copolymer derived from an α-hydroxycarboxylic acid.

13. The method according to claim 12, wherein the copolymer is a lactic acid—glycolic acid copolymer.

14. A sustained-release preparation, which is produced by permitting a water-soluble polypeptide in an aqueous solution to permeate into a biodegradable matrix.

15. A sustained-release preparation, which is produced by mixing a biodegradable polymer and a water-soluble metal salt of an aliphatic carboxylic acid, and permitting a water-soluble polypeptide in an aqueous solution to permeate into the resulting biodegradable matrix produced by the mixing of the biodegradable polymer and the water-soluble metal salt of the aliphatic carboxylic acid.

16. The sustained-release preparation as claimed in claim 14, wherein the preparation is for injection.

17. The method as claimed in claim 1, wherein the water-soluble polypeptide permeates into the biodegradable matrix without contacting an organic solvent.

18. The sustained-release preparation as claimed in claim 14, wherein the water-soluble polypeptide has permeated into the biodegradable matrix without contacting an organic solvent.

19. The sustained-release preparation as claimed in claim 15, wherein the water-soluble polypeptide has permeated into the biodegradable matrix without contacting an organic solvent.

* * * * *